United States Patent
Sudoh et al.

(10) Patent No.: US 7,211,380 B1
(45) Date of Patent: May 1, 2007

(54) PHYSIOLOGICALLY ACTIVE POLYPEPTIDE AND DNA

(75) Inventors: Tetsuji Sudoh, Tokyo (JP); Keiji Maekawa, Tokyo (JP); Naoto Minamino, Miyazaki-gun (JP); Kenji Kangawa, Miyazaki-gun (JP); Hisayuki Matsuo, 6-4-24-204, Okamoto, Higashinada-ku, Kobe-shi, Hyogo (JP); Atsushi Izumi, Tokyo (JP); Mika Takashima, Tokyo (JP)

(73) Assignees: Shionogi & Co., Ltd., Osaka (JP); Hisayuki Matsuo, Kobe-shi (JP)

( * ) Notice: Subject to any disclaimer, the term of this patent is extended or adjusted under 35 U.S.C. 154(b) by 0 days.

(21) Appl. No.: 08/192,800

(22) Filed: Feb. 7, 1994

Related U.S. Application Data

(63) Continuation of application No. 07/855,475, filed on Mar. 23, 1992, now abandoned, which is a continuation of application No. 07/486,827, filed on Mar. 1, 1990, now abandoned.

(30) Foreign Application Priority Data

Mar. 1, 1989 (JP) .................................. 1-49636
Mar. 10, 1989 (JP) .................................. 1-59183

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/23.5

(58) Field of Classification Search .............. 435/6, 435/69.1, 320.1; 536/23.1, 23.5
See application file for complete search history.

(56) References Cited

U.S. PATENT DOCUMENTS

| | | | | |
|---|---|---|---|---|
| 4,478,829 A | * | 10/1984 | Landaburu et al. | 514/21 |
| 4,503,039 A | * | 3/1985 | Kotitschke et al. | 424/530 |
| 4,599,227 A | * | 7/1986 | Dees et al. | 424/450 |
| 5,114,923 A | * | 5/1992 | Seilhamer et al. | 514/12 |
| 5,674,710 A | * | 10/1997 | Seilhamer et al. | 435/69.4 |
| 5,948,761 A | * | 9/1999 | Seilhamer et al. | 514/12 |

FOREIGN PATENT DOCUMENTS

| | | |
|---|---|---|
| EP | 0 246 795 | 11/1987 |
| JP | 63-107997 | 5/1988 |
| WO | WO 85/04872 | 11/1985 |
| WO | 8912069 | 12/1989 |

OTHER PUBLICATIONS

Sudoh et al. 1988 Nature 332:78.*
Suggs et al 1981 Proc. Natl. Acad. Sci USA 78:6613.*
Maniatis et al. Molecular Cloning: A Lab. Manual, CSH 1982, pp. 405-443, 226-227.*
Sudoh et al. Nature 332:78-81, 1988.*
Sudoh et al. Biochem Biophys. Res Comm. 159:1427-1434, 1989.*
Vlasuh et al. Biochem Biophys. Res Comm. 136:396-403, 1986.*
Oikawa et al. Biochem Biophys. Res Comm. 132:892-899, 1985.*
Maekawa et al. Biochem Biophys. Res Comm. 157:410-416, 1988.*
Sudoh et al. Biochem Biophys. Res. Comm. 155:726-732, 1988.*
Maniatis et al. "Molecular Cloning: a Laboratory Manual", Cold Spring Harbor Lab., CSH, N.Y., 1982 p. 228.*
Biochemical and Biophysical Research Communications, vol. 159, No. 3 Mar. 1989, pp. 1427-1434, T. Sudoh, et al.
FEBS Letters, vol. 259 No. 2, Jan. 1990, p. 341-375, Y. Kambayashi, et al.
Biochemical and Biophysical Research Comm. vol. 155 Sep. 1988, Ueda, et al.
Biochemical & Biophysical Research Comm. vol. 157, No. 1 Nov. 1988 p. 402-409, N. Minamino, et al.
J. Gordon Porter et al., Cloning of a cDNA Encoding Porcine Brain Natriuretic Peptide, *The Journal of Biological Chemistry*, vol. 264, No. 12, pp. 6689-6692, Nov. 15, 1988.

* cited by examiner

*Primary Examiner*—Sean McGarry
(74) *Attorney, Agent, or Firm*—Oblon, Spivak, McClelland, Maier & Neustadt, P.C.

(57) ABSTRACT

A physiologically active polypeptide derived from human brain and a DNA fragment comprising the base sequence encoding the polypeptide are disclosed. The polypeptide possesses excellent smooth muscle relaxation activity, diuretic or natriuretic activity, and vasodepressor activity, and is thus useful as a medicine for curing circulation diseases, e.g. cardiac edema, nephric edema, hepatic edema, pulmonary edema, hypertension, congestive heat failure, and acute and chronic renal failure.

2 Claims, 3 Drawing Sheets

FIG. 2

```
                                                                                                                    -1
     GCCAGGGCTGAGGGCAGTGGGAAGCAAACCCGACGCATCGCAGCAGCAGCAGCAGCACCAGCAGCCTCCCAGTCCCTCCAGAGAC

90
ATG GAT CCC CAG ACA GCA CCT TCC CGG GCG CTC CTG CTC TTC TTG CAT CTG GCT TTC CTG GGA GGT TCC CAC CCG CTG GGC
Met Asp Pro Gln Thr Ala Pro Ser Arg Ala Leu Leu Leu Phe Leu His Leu Ala Phe Leu Gly Gly Ser His Pro Leu Gly

180
AGC CCC GGT TCA GCC CTC TCG GAC TTG GAA ACC TCC GGG TTA CAG GAG CAG CGC AAC CAT TTG CAG GGC AAA CTG TCG GAG GTG GAG
Ser Pro Gly Ser Ala Ser Leu Asp Leu Glu Thr Ser Gly Leu Gln Glu Gln Arg Asn His Leu Gln Gly Lys Leu Ser Glu Val Glu

270
CAG ACA TCC CTG GAG CCC CTC GAG CAG AGC CCC CGT CCC ACA GGT GTC TGG AAG TCC CGG GAG GTA GCC ACC GAG GGC ATC CGT GGC CAC
Gln Thr Ser Leu Glu Pro Leu Glu Gln Ser Pro Arg Pro Thr Gly Val Trp Lys Ser Arg Glu Val Ala Thr Glu Gly Ile Arg Gly His

360
CGG AAA ATG GTC CTC TAC ACC CTG CGG GCA CCA CGA AGC CCC AAG ATG GTG CAA GGG TCT GGC TCC TTT GGG AGG AAG ATG GAC CGG ATC
Arg Lys Met Val Leu Tyr Thr Leu Arg Ala Pro Arg Ser Pro Lys Met Val Gln Gly Ser Gly Cys Phe Gly Arg Lys Met Asp Arg Ile

465
AGC TCC TCC AGT GGC CTG GGC TGC AAA GTG CTG GGC AGG CGG CAT TAAGAGGAAGTCCTGGCTGCAGACACCTGCTTCTGATTCCACAAGGGCTTTTTCCTCAACCC
Ser Ser Ser Ser Gly Leu Gly Cys Lys Val Leu Gly Arg Arg His

584
TGTGGCGCCCTTTGAAGTGACTCATTTTTTAATGTATTCATTGTATTTATTTGATTGTTTATATAAGATGCTTTCTTACCTTTGAGGACAAAATTTCCACGGTGAAATAAAGTCAACA

593
TTTATAAGCT
```

FIG. 3-A
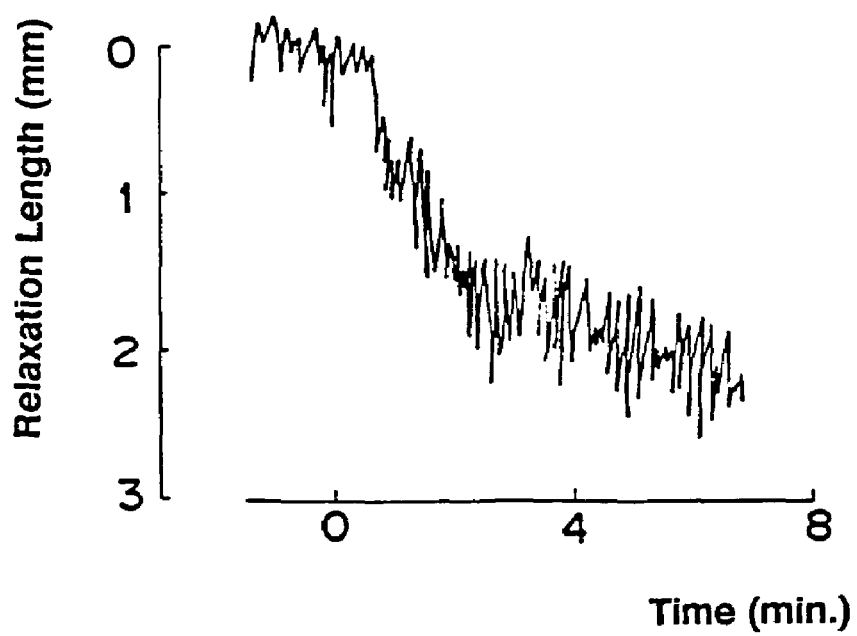
FIG. 3-B
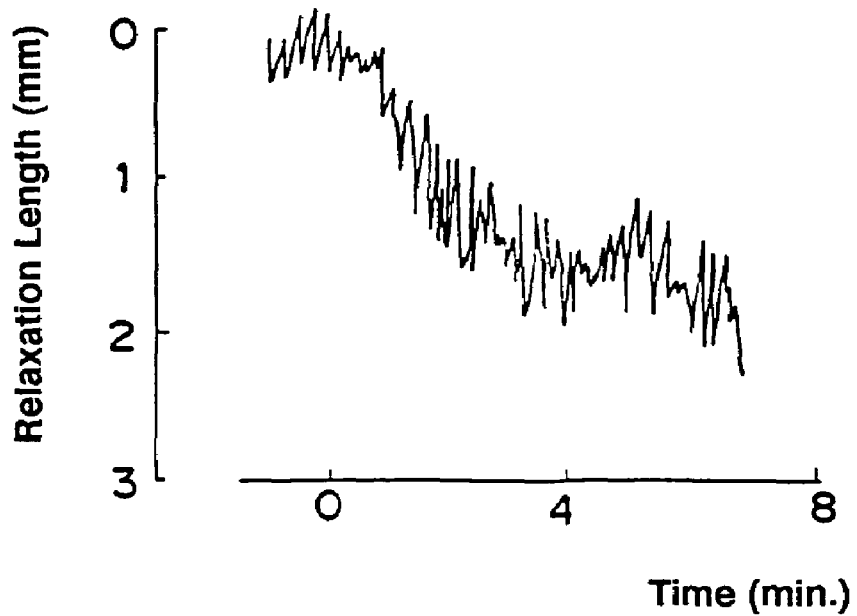

PHYSIOLOGICALLY ACTIVE POLYPEPTIDE AND DNA

The present application is a continuation of application Ser. No. 07/855,475, filed Mar. 23, 1992, abandoned, which is a continuation of application Ser. No. 07/486,827, filed Mar. 1, 1990, abandoned.

BACKGROUND OF THE INVENTION

1. Field of the Invention

This invention relates to a physiologically active polypeptide, a DNA encoding the polypeptide, and a pharmaceutical composition for treating and curing circulation diseases comprising the polypeptide as an effective ingredient.

2. Description of the Background Art

Structures of new polypeptides secreted by human or rat atrium and having natriuretic activity have successively been determined and reported in the years 1983–1884 [*Biochem. Biophys. Res. Commun.* 117, 859 (1983); *Biochem. Biophys. Res. Commun.* 118, 131–139 (1984)]. These polypeptides were named artium natriuretic peptides (hereinafter referred to as "ANP"). Since they have strong natriuretic activity as well as relaxing activity of vessel and smooth muscle, they are attracting much attention as a new peptide medicine for circulation disease.

In 1988, a new peptide having diuretic activity was isolated in a purified form from porcine brain. Its structure was determined and the peptide was named "porcine brain natriuretic peptide" (hereinafter referred to as porcine BNP or pBNP) [*Nature*, 332, No. 6159, 78–81 (1988); *Biochem. Biophys. Res. Commun.* 155, 726–732 (1988)]. Pharmaceutical activities of pBNP resemble those of ANP, and include diuretic activity, natriuretic activity, vasodepressor activity, chicken rectum relaxation activity, and the like. The specific activities of pBNP also resemble those of ANP, except that the rectum relaxation activity of pBNP is 3 to 4 times higher than that of ANP. This is the reason that pBNP is expected to be a new medicine for circulation disease and that studies involving DNA of porcine BNP are being undertaken. Cloning of cDNA possessing a base sequence encoding porcine BNP and its precursor has been reported [*Biochem. Biophys. Res. Commun.* 157 (1), 410–416 (1988)].

Development of brain natriuretic peptide derived from human being (hereinafter referred to as human BNP or hBNP) has been desired as a therapeutic agent for human circulation diseases. Such a peptide, however, has not been heretofore found. Nor has its structure been clarified neither on a DNA level nor on a peptide or protein level.

In view of this situation, the present inventors have conducted extensive studies to obtain human BNP, and have been successful in cloning cDNA encoding human BNP by screening a cDNA library.

Furthermore, the present inventors have synthesized various human BNPs based on the amino acid sequence deduced from the cDNA base sequence and have studied their pharmacological activities. As a result, the inventors have found that these BNPs had excellent smooth muscle relaxation and natriuretic activities.

SUMMARY OF THE INVENTION

Accordingly, an object of this invention is to provide a DNA fragment comprising a base sequence encoding a polypeptide derived from human brain and possessing natriuretic activity.

Another object of the present invention is to provide a pharmaceutical composition for curing circulation diseases which comprise as an effective ingredient a physiologically active polypeptide represented by the formula (I),

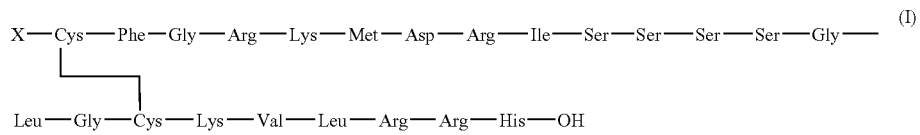

wherein X is H, H-Gly-Ser-Gly-, or H-Ser-Pro-Lys-Met-Val-Gln-Gly-Ser-Gly-.

Other objects, features and advantages of the invention will hereinafter become more readily apparent from the following description.

BRIEF DESCRIPTION OF THE DRAWINGS

FIG. 2 shows the cDNA base sequence and the amino acid sequence deduced from the base sequence which was determined by the strategy shown in FIG. 1.

The FIG. 3-A shows the change in relaxation length with time of a chicken rectum specimen to which human BNP-26 of the present invention was administered. FIG. 3-B shows the change in relaxation length with time of a chicken rectum specimen to which human BNP-26 of the present invention was administered.

DETAILED DESCRIPTION OF THE INVENTION AND PREFERRED EMBODIMENTS

Figure 1:
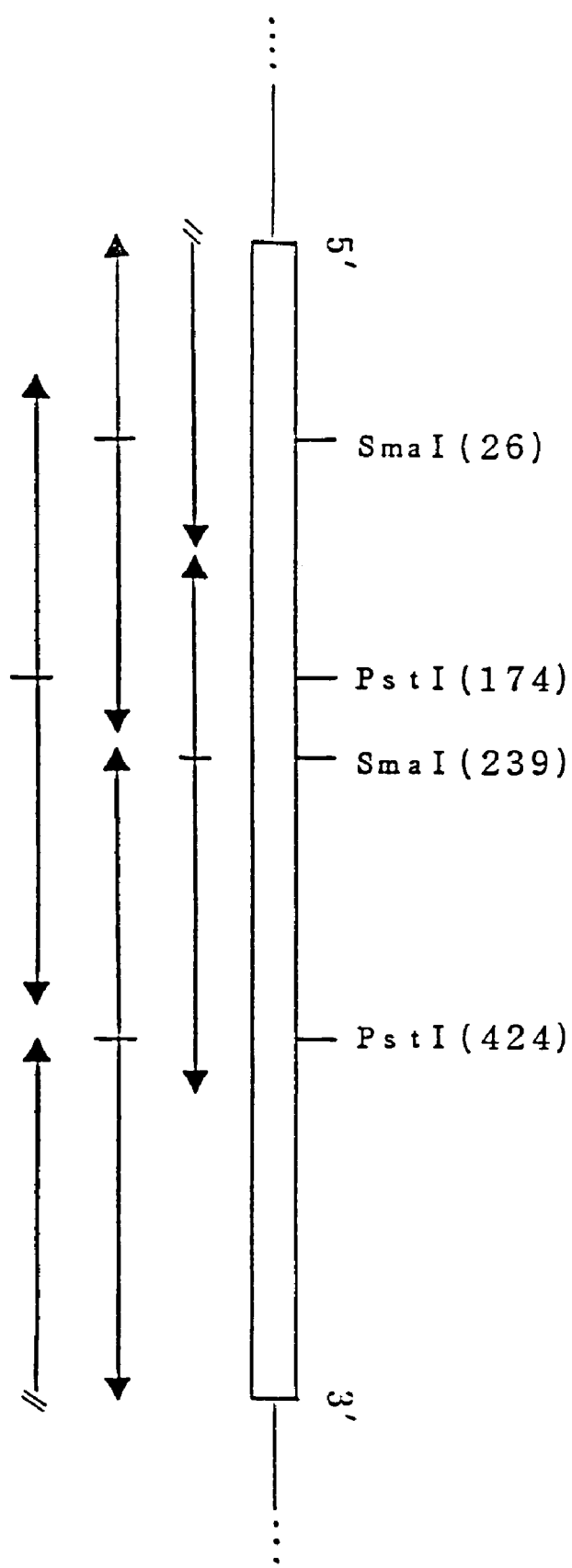
FIG. 1 shows the base sequence determination strategy of cDNA fragment inserted into positive clone hBNP-57 and the restriction endonuclease map of the cDNA.

In this specification, the peptide of formula (I) having H for X may be referred to as human BNP-23, that having H-Gly-Ser-Gly- for X may be referred to as human BNP-26, and that having H-Ser-Pro-Lys-Met-Val-Gln-Gly-Ser-Gly- for X may be referred to as human BNP-32.

The DNA fragment of the present invention can be prepared, for example, by the following process.

The total RNA is separated from a human tissue which is considered to contain human BNP. mRNA is isolated from the total RNA and a cDNA library is constructed by a conventional method. A DNA fragment encoding human BNP can be isolated by screening the cDNA library by means of hybridization with a probe which has DNA sequence encoding a part of porcine BNP. The process is illustrated in more detail.

(1) Construction of cDNA Library

The mRNA is prepared from tissue such as human brain, human atrium, or the like. The RNA can be separated by homogenizing a human atrium, for example, by homogenizing the atrium together with guanidylthiocyanate, followed by equilibrated density gradient ultracentrifugation using cesium trifluoro acetate. The mRNA is purified according to a conventional manner using oligo (dT) cellulose column chromatography. Synthesis of cDNA from the mRNA is carried out according to a conventional method, e.g. the method using a cDNA synthesis kit (manufactured by Pharmacia Co.), the Okayama-Berg method (*Mol. Cell. Biol.* 2, 161–170, 1982), the method of Gubler, U. and Hoffman, B. J. (*Gene,* 25, 263–269 (1983) or its modification, or a method using other commercially available kit. An endonuclease EcoRI adaptor is applied to cDNA thus obtained, following which the 5'-end is phosphorylated using T-4 polynucleotide kinase or the like. The cDNA library is then constructed by ligation using a vector, e.g. gt10, followed by in vitro packaging using, for example, Gigapack Gold (trademark: manufactured by Stratgene Co.).

(2) Screening of Human BNP Clone

Screening of human BNP clone is carried out using a labeled porcine cDNA fragment as a probe. This cDNA fragment is, for example, a 120 bp fragment which is obtained by the digestion of the complete clone or the incomplete clone obtained in the course of cDNA cloning of the porcine BNP using endonucleases XhoI and RsaI [*Biochem. Biophys. Res. Commun.* 157, 410 (1988)]. The 120 bp fragment comprises DNAs encoding the active portion of the porcine BNP (BNP-26) consisting of 26 amino acids and its upstream 30 bp. A probe to be used is prepared by labeling this cDNA fragment with $^{32}$P. The probe and the cDNA library prepared in (1) above are hybridized and the positive clone is selected. The DNA fragment encoding human BNP can be prepared by cleaving the selected positive clone with a suitable endonuclease.

To determine the base sequence of the DNA fragment thus obtained the following conventional method is used, for example, by incorporating the DNA fragment into a vector for sequencing, preparing a restriction endonuclease map of the cDNA region, and further incorporating DNA fragments produced by using endonucleases which can cut the DNA into a suitable length into a vector for sequencing to obtain a subclone, and determining the whole base sequence by the method of Sanger et al. [*Proc. Natl. Acad. Sci. USA,* 74, 5463–5469 (1977)].

The base sequence of the DNA fragment encoding human BNP thus determined and the amino acid sequence of the human BNP are shown in FIG. 2. In the base sequence in FIG. 2, the sequence 1–402 is considered to code for pre-pro-human BNP which is comprised of 134 amino acids, and 79–402 of these bases are considered to code for pro-human BNP which is comprised of 108 amino acids. These supposition were based on the fact that the structure of the signal peptide located before the precursor is very similar to that of porcine, and that the porcine BNP also has the amino acid sequence Arg-Ser-His-Pro-Leu-Gly corresponding to the base numbers 73–90 and the Ser-His bond of this sequence is cut to form the porcine BNP precursor [*Biochem. Biophys. Res. Commun.* 157, 410 (1988)]. Among these, sequence 307–402 is considered to encode the human BNP-32 which is comprised of 32 amino acids. The precursor is considered to form the human BNP-32 as a result of the processing, although this is not decisive because the human BNP has never been successfully isolated as a peptide. Of porcine DNAs, porcine BNP-26 [*Nature,* 332, 78–81 (1988)] and porcine BNP-32 consisting of 32 amino acids [*Biochem. Biophys. Res. Commun.* 155, 726–732 (1988)] have been isolated. As for ANP, human αANP consisting of 28 amino acids from human tissue [*Biochem. Biophys. Res. Commun.* 118, 131–139 (1984)] and rat αANP consisting of 28 amino acids from rat tissue [*Biochem. Biophys. Res. Commun.* 117, 859–865 (1983)] have been isolated. All of them are produced by the processing which took place downstream of Arg and Pro-Arg existing in the precursor. In the case of human BNP, since an Arg preceding the peptide having 23 amino acids from Cys (112) to His (134) which is considered to exhibit activity is the 102 Arg and this Arg has a Pro-Arg structure, the human BNP-32 consisting of 32 amino acids is presumed to be produced as a result of the processing after the Pro-Arg structure.

Based on the fact that the ANP precursor had been found to have a physiological activity, the human BNP precursor is also considered to have some physiological activity. Thus, both the human BNP-32 and the precursor are useful as a medicine.

The DNA corresponding to the base number 1–402 and the amino acid sequence deduced from the base sequence are as shown in FIG. 2. Peptides which exhibit the activity is not necessarily limited to the whole peptide produced from the DNA corresponding to the base number 1–402. For example, a peptide having a shortened C-terminal is useful. It is also possible to replace a portion of the DNA fragment by other codons encoding amino acids to produce a peptide having the activity as human BNP. The DNA sequence coding for these amino acids is not limited one specific sequence. Once the DNA fragment of the whole length is specified, a number of variant DNAs can be produced, and a peptide having activity can be produced using these variant DNAs. The peptides of the present invention, therefore, are not limited to those deduced from the human-derived DNA of the whole length, but include those having the activity as that of the human BNP. The DNA fragment of the present invention is that having the base sequence encoding such a peptide.

A variety of peptides, including human BNP-32, pro-human BNP, and other peptides having a biological activity with the human-BNP-32 or its precursor, can be prepared by using the DNA fragment of the present invention and introducing an expression vector.

It should be understood that the peptides having a somewhat different amino acid sequence should be included in the peptide of the present invention, so long as such peptides possess the activity as that of human BNP.

The peptide of the present invention which is represented by formula (I) can also be prepared by the solid phase method or the liquid phase method which are conventionally used in the art [e.g. N. Izumiya, et al. "Peptide Synthesis", Maruzen Publishing Co., Ltd. (1984); "Lecture of Biochemistry Experiment (I), Protein Chemistry" edited by Chemical Society of Japan, vol. 1, 208–495 (1977), published by Tokyo Kagaku Dojin].

When the peptide (I) is prepared by the solid phase method, the following protective groups of amino acid can preferably be used; i.e., 9-fluorenylmethyloxycarbonyl (Fmoc) group for the α-amino group, tert-butyl (tBu) group for the β-carboxyl group of aspartic acid, 4-methoxy-2,3,6-trimethylbenzenesulfonyl (Mtr) group for the guanidino group of arginine, tert-butyl (tBu) group for the hydroxyl group of serine, acetamidomethyl (Acm) group for the thiol group of cysyeine, trityl group (Trt) for the imidazole group of histidine, and tert-butyloxycarbonyl (Boc) group for the ε-amino group of lysine. p-Alkoxybenzyl alcohol resin (Wang Resin) is a preferable insoluble resin for use. Preferable methods used for the condensation of protected amino acids are the dicyclohexylcarbodiimide (DCC) method, the active ester method using 1,3-diisopropylcarbodiimide (DIC), the acid anhydride method using DCC, the diphenylphosphoryl azide (DPPA) method, and the like. The protective groups are not limited to those given above. α-amino group of amino acids, for example, may be protected by tert-butyloxycarbonyl (Boc) group.

Production of the polypeptide of the present invention by the solid phase method can be carried out, for example, by the following manner. The protected derivative Fmoc-His(Trt)-OH in which His is the C-terminal amino acid of the polypeptide is first introduced into p-alkoxybenzyl alcohol resin. The corresponding protected amino acids are successively combined in this way to synthesize a protected peptide resin. Subsequently, removal of peptide from the resin and elimination of protective groups other than Acm are concurrently performed by the treatment with piperidine and trifluoroacetic acid (TFA), the treatment with piperidine and trimethylsilyl bromide (TMSBr) [*Chem. Pharm. Bull.,* 35, (9), 3880 (1987)], and the like to obtain a peptide having an Acm group for thiol of cystein, such a peptide being referred to as Cys(Acm)-peptide. Then, the Cys(Acm)-peptide is oxidized with iodine to remove the thiol protective group and, at the same time, to form a disulfide bond between two thiol groups of cystein in the peptide molecule, thus producing crude polypeptide of the present invention.

The crude polypeptide is purified by a conventional manner such as, for example, gel filtration, ion exchange chromatography, reversed phase HPLC, or the like.

The peptide of formula (I) of the present invention can be converted into an acid addition salt according to a conventional manner using an inorganic acid such as hydrochloric acid, sulfuric acid, phosphoric acid, or the like; or an organic acid such as formic acid, acetic acid, citric acid, tartaric acid, fumaric acid, maleic acid, or the like.

The peptide of formula (I) of the present invention thus produced possesses smooth muscle relaxation and other activities.

<Smooth Muscle Relaxation Activity>

(1) Test Method

Rectum of a chicken, age 4–7 days, was enucleated and muscle specimens, 1.5 cm long, were prepared. The specimens were immersed into 2.5 ml of Krebs-Henseleit solution, containing $2 \times 10^8$ M carbachol, which was aerated with a 95% $O_2$–5% $CO_2$ mixed gas and maintained at 32° C. in a 3 ml organ bath. The specimens were allowed to equilibrate for about 30 minutes. When the self-acting of the muscle became constant, 100 ng of human BNP-26 was added and relaxation of the muscle was measured for 6–8 minutes after the addition. After the measurement, the specimens were rinsed two or three times, and, after 20–30 minutes, the above procedure was repeated using 200 ng of human BNP-32. The human BNPs were used dissolved in a prescribed amount of physiological saline. Isotonic relaxations of the muscles under a tension of 0.5 g were registered on a kymograph (KN-259: trademark, product of Natsumeseisakusyo Co.)

(2) Results

The results are shown in FIGS. 3-A and 3-B. From the results, the polypeptide of the present invention was found to exhibit strong smooth muscle relaxation activity at a dose of 100–200 ng.

As mentioned above, the human BNP produced by the present invention possesses excellent smooth muscle relaxation activity, diuretic or natriuretic activity, and vasodepressor activity. The BNP is safe as a medicine for humans because it is derived from human, thus it can be used as a medicine for curing such diseases as cardiac edema, nephric edema, hepatic edema, pulmonary edema, hypertension, congestive heat failure, acute and chronic renal failure, and the like.

Any methods conventionally used for the administration of peptide medicines, e.g. intravenous injection, intramuscular injection, subcutaneous injection, sublingual administration, intracutaneous administration, rectum administration, or the like, can be employed for the administration of the peptide of the present invention.

A preferable dose is 0.5 μg/kg to 100 mg/kg, with the especially preferable range being 0.5 μg/kg to 1 mg/kg.

Other features of the invention will become apparent in the course of the following description of the exemplary embodiments which are given for illustration of the invention and are not intended to be limiting thereof.

EXAMPLES

Example 1

(1) Construction of cDNA Library

Human atrium (3 g) was pulverized by a treatment with with liquid nitrogen. To this was added, according to the method of Chirgwin et al. [Chirgwin, J. W. et al. *Biochemistry*, 18, 5294–5299 (1979)], a guanidiumthiocyanate aqueous solution, and the mixture was homogenized. The whole RNA was separated by equilibrium density gradient ultracentrifugation using cesium trifluoro acetate, following which the RNA was purified, according to a conventional method, by oligo (dT) cellulose column chromatography to isolate 37 μg of poly(A)$^+$RNA(mRNA).

cDNA was synthesized from 3 μg of mRNA by using a cDNA synthesis kit (product of Pharmacia Co.). After the addition of an EcoRI adaptor, the 5'-end was phosphorylated with T4 polynucleotide kinase and ligation was carried out using λgt10 as a vector. λgt10 arms which was digested by EcoRI and dephosphorylated was employed as a vector. For 2 μg of the λgt10, the amount of cDNA used for the ligation was 0.1 μg converted to the amount of RNA used for the cDNA synthesis. After the ligation, the product was packed using a packaging kit (Gigapack Gold, product of Stratgene Co.), and cDNA library was obtained.

A small amount of cDNA was inoculated into *E. coli* c600 and c600hfl in order to investigate the completeness of the cDNA library. As a result, it was found that among the plaque produced by *E. coli* c600, 90% was transparent and 10% was turbid, evidencing that the share of the recombinant phage in the library was 90%. Furthermore, the number of plaques in the whole cDNA library was found to be $7 \times 10^7$.

(2) Screening of Human BNP Clone

Screening was carried out on $5 \times 10^5$ plaques expressed by inoculating a portion of cDNA library into *E. coli* c600hfl. The cDNA fragment encoding porcine BNP, which was labeled with $^{32}$P, was used as a probe for the screening. The cDNA fragment was prepared from plasmid BNP-82 (320 bp) which is an incomplete clone obtained in the course of cDNA cloning of the porcine BNP [*Biochem. Biophys. Res. Commun.* 157, 410 (1988)], and plasmid BNP-82 was digested by restriction endonucleases XhoI and RsaI to obtain a 120 bp fragment which consists of a DNA fragment encoding porcine BNP-26 and its upstream 30 bp. The 120 bp fragment was then purified by acrylamide gel electrophoresis.

Plaques were first transferred to a nylon filter, and neutralized after alkali treatment, following which DNA was fixed by UV irradiation. The filter was immersed into a 5× Denhardts solution and a 4×SSC solution of 0.6 M NaCl and 0.06 M sodium citrate containing 100 µg/ml of denatured salmon sperm DNA and 0.1% SDS at 60° C. for 3 hours, thus effecting hybridization. A probe labeled with $^{32}$P by a Random primed DNA labeling kit (Product of Belinger Manheim Co.) was added to the hybridization solution having the same composition as the prehybridization solution to a concentration of $2\times10^6$ cpm/ml, wherein the filter was incubated overnight at 60° C.

The filter was then washed with a 2×SCC solution containing 0.1% SDS, dried in the air, and submitted to autoradiography.

Fifty five (55) hybridization positive plaques were thus obtained. The 55 positive plaques were submitted to a test to detect whether they could hybridize using the DNA (680 bp) encoding human ANP as a probe, and were found that all were negative. This is an evidence that this cDNA is different from the known cDNA encoding human ANP. The above 55 positive plaques were monocloned and λ-phage DNA was prepared according to a conventional method. A DNA fragment obtained by cleaving the λ-phage DNA with the restriction endonulease EcoRI was investigated and was found that a cDNA having a maximum length of about 700 bp was inserted into a clone which was named λhBNP-57. This insert cDNA was incorporated into Blue Script (KS (+)) (product of Stratgene Corp.) which is a sequencing vector, thus producing phBNP-57. The *E. coli* containing this plasmid was named *E. coli* HB101/phBNP-57 and deposited with Fermentation Research Institute, Agency of Industrial Science and Technology (Deposition No. 2299, FERM BP-2299). A restriction endonulease map of the cDNA region was prepared. cDNA fragments were prepared using suitable restriction endonuleases which could cut the cDNA into a suitable length and these fragments were again incorporated into the blue script and subcloned. FIG. 1 shows the restriction endonuclease cleaving sites of the cDNA region and the base sequence determination strategy. The base sequence was determined by the method of Sanger et al. [*Proc. Natl. Acad. Sci., USA,* 74, 5463–5467 (1977)].

FIG. 2 shows the cDNA base sequence and the amino acid sequence corresponding to the base sequence.

The inserted DNA sequence has a long translational region starting from a translation initiation codon, ATG, and ending a translation termination codon, TAA. The cDNA having the whole length of 692 bp is considered to have a 5'-side non-translational region of the base pair number –99 to –1, 1–78 codes for a signal peptide, and 79–402 codes for the human BNP precursor. Among these, 307–402 are considered to codes for the human BNP-32 consisting of 32 amino acids 403–593 are a non-translational region.

The amino acid sequence corresponding to the base sequence of 307–402 encoding the human BNP-32 has a cyclic structure which is formed with the cysteine disulfide bond of 17 amino acids and is very similar to porcine BNP.

Example 2

A pro-human-BNP-producing vector can be obtained by using phBNP-57 clone, a recombinant plasmid which is constructed by insertion of a cDNA obtained by digestion of λphBNP-57 with the restriction endonuclease EcoRI into a plasmid blue script. More specifically, a new restriction endonuclease recognition site and a translation initiation codon (ATG) can be introduced at the site immediately preceding the pro-human-BNP-code region of phBNP-57 by site-directional mutation. A fragment is isolated by the utilization of this new recognition site. The above fragment is then inserted into the expression vector at immediately downstream of the plasmid promoter, and the plasmid is inserted into *E. coli*. The *E. coli* is cultured with nutrients sufficient to synthesize polypeptide followed by which pro-human BNP is collected. Another method of obtaining the human BNP-32 or the fragment to be cultured by *E. coli* is changing the site of site-directional mutation and the base sequence on the inserted cDNA of phBNP-57. The human BNP-32 or the fragment is then inserted into the expression vector and the vector is introduced into *E. coli* The human BNP-32 or the human BNP is obtained from the cultured *E. coli*.

Example 3

(1) Synthesis of Peptide Human BNP-26 and Human BNP-32

(a) Synthesis of a Protected Peptide Resin

For the synthesis of the protected peptide resin all α-amino groups of amino acids were protected by 9-fluorenylmethyloxycarbonyl (Fmoc) group, and among active side chains, the β-carboxyl group of aspartic acid was protected by tert-butyl (tBu) group, the guanidino group of arginine was protected by 4-methoxy-2,3,6-trimethylbenzenesulfonyl (Mtr) group, the hydroxyl group of serine was protected by tert-butyl (tBu) group, the thiol group of cysteine was protected by acetamidomethyl (Acm) group, the imidazole group of histidine was by trityl group (Trt), and the ε-amino group of lysine was by tert-butyloxycarbonyl (Boc) group. 1.0 g of p-alkoxybenzyl alcohol resin into which Fmoc-His(Trt) group was introduced was used as the resin.

In the condensation of the protected amino acid, the Fmoc group which is the protected group for the N-terminal amino acid of the protected peptide bonding to the resin was almost completely removed by the treatment with piperidine, repeated twice, at room temperature for 6 minutes. The free amino group from which the Fmoc group was eliminated was condensed with the carboxyl group of the Fmoc protected amino acid located next in the sequence of the target peptide. The condensation of the protected amino acid was carried out by treating 1 mmol of Fmoc-protected amino acid with 1,3-diisopropylcarbodiimide (DIC) in the presence of 1-hydroxybenztriazole. The same procedure was repeated when the reaction was not completed by this treatment. The progress and completion of the reaction were monitored by the Keizer test using ninhydrin.

Fmoc-Gly-Ser(tBu)-Gly-Cys(Acm)-Phe-Gly-Arg(Mtr)-Lys(Boc)-Met-Asp(tBu)-Arg(Mtr)-Ile-Ser(tBu)-Ser(tBu)-Ser(tBu)-Ser(tBu)-Gly-Leu-Gly-Cys(Acm)-Lys(Boc)-Val-Leu-Arg(Mtr)-Arg(Mtr)-His(Trt)- resin was thus synthesized. At this stage, a portion of the product was taken out and the Fmoc group was removed in the same manner as described above, thus obtaining 670 mg of H-Gly-Ser(tBu)-Gly-Cys(Acm)-Phe-Gly-Arg(Mtr)-Lys(Boc)-Met-Asp (tBu)-Arg(Mtr)-Ile-Ser(tBu)-Ser(tBu)-Ser(tBu)-Ser(tBu)-Gly-Leu-Gly-Cys(Acm)-Lys(Boc)-Val-Leu-Arg(Mtr)-Arg (Mtr)-His(Trt)- resin (hereinafter referred to as "protected human BNP-26 resin").

The remaining resin was further subjected to N-terminal extension reaction to obtain Fmoc-Ser(tBu)-Pro-Lys(Boc)-Met-Val-Gln-Gly-Ser(tBu)-Gly-Cys(Acm)-Phe-Gly-Arg (Mtr)-Lys(Boc)-Met-Asp(tBu)-Arg(Mtr)-Ile-Ser(tBu)-Ser (tBu)-Ser(tBu)-Ser(tBu)-Gly-Leu-Gly-Cys(Acm)-Lys (Boc)-Val-Leu-Arg(Mtr)-Arg(Mtr)-His(Trt)- resin. The Fmoc group was removed in the same manner as described above, thus obtaining 1.5 g of H-Ser(tBu)-Pro-Lys(Boc)-Met-Val-Gln-Gly-Ser(tBu)-Gly-Cys(Acm)-Phe-Gly-Arg (Mtr)-Lys(Boc)-Met-Asp(tBu)-Arg(Mtr)-Ile-Ser(tBu)-Ser (tBu)-Ser(tBu)-Ser(tBu)-Gly-Leu-Gly-Cys(Acm)-Lys (Boc)-Val-Leu-Arg(Mtr)-Arg(Mtr)-His(Trt)- resin (hereinafter referred to as "protected human BNP-32 resin").

(b) Synthesis of Cys(Acm)-Human BNP-26

The protected human BNP-26 resin (600 mg) was deprotected with 2.4 ml of thioanisole, 20 ml of trifloroacetic acid (TFA), 2.6 ml trimethylsilyl bromide (TMSBr), and 340 µl of ethanedithiol at 0° C. for 3 hours. After the reaction, the resultant reaction mixture was washed with 200 ml of ether to remove anisole, and the product was extracted with 20 ml of 1 N acetic acid. The resin and the insoluble substance was removed by centrifugation. To the residue was added 1 ml of 1 M sodium fluoride (NaF) with cooling. The mixture was adjusted to pH 8 with 5% aqueous ammonia using a Universal test paper and left for 30 minutes. After adjusting to pH 5 with 1 N acetic acid, the mixture was diluted with water to a volume of 10-fold, absorbed to a column (φ3 cm×8.5 cm) packed with 60 ml of ODS resin (LC-Sorb: trademark, product of Chemco Co.), washed thoroughly with 0.1 N acetic acid, and eluted with 200 ml of 60% acetonitrile containing 0.1% TFA. The acetonitrile was evaporated under reduced pressure and the residue was freeze-dried to obtain 300 mg of crude Cys(Acm)-human BNP-26.

The crude product was dissolved into 9 ml of 1 N acetic acid and the solution was subjected to reversed phase HPLC over a nucleosil 120-5C18 column (20×250 mm) in 9 portions at a flow rate of 5 ml/min. Solvent (A), a mixture of water:acetonitrile:10% TFA=90:10:1, and Solvent (B) a mixture of water:acetonitrile:10% TFA=40:60:1, were used at a linear gradient from (A):(B)=90:10 to (A):(B)=55:45 for 120 minutes. This procedure was repeated 9 times and the main peak eluted at 57–61 minute was collected. Acetonitrile was evaporated from the collected fraction and the residue was freeze-dried to obtain 96.0 mg of Cys(Acm)-human BNP-26.

(c) Synthesis of Human BNP-26

Solution A was prepared by dissolving 227 mg of iodine into 50 ml of 95% acetic acid and by adding 80 µl of 1 N hydrochloric acid.

Solution B was prepared by dissolving 2.1 g of citric acid and 575 mg of L-ascorbic acid into 10 ml of 2 N sodium hydroxide, and made up to the final volume of 50 ml by an addition of water.

A solution 89.0 mg of Cys(Acm)-human BNP-26 in 5 ml of 90% acetic acid was added dropwise into 30 ml of Solution A at room temperature while stirring. After the addition, the mixture was stirred for a further 20 minutes. To this mixture Solution B was added dropwise until the brown color of iodine disappeared. The resulting solution was diluted with 500 ml of water and applied to a column (φ2 cm×9.5 cm) packed with 30 ml of ODS resin (LC-Sorb: trademark, product of Chemco Co.). The column was washed thoroughly with 0.1 N acetic acid, and eluted with 60 ml of 60% acetonitrile containing 0.1% TFA. The acetonitrile was evaporated under reduced pressure and the residue was freeze-dried to obtain 60.0 mg of crude human BNP-26.

The crude product was dissolved into 4 ml of 1 N acetic acid and the solution was applied to reversed phase HPLC over a nucleosil 120-5C18 column (20×250 mm) in 4 divided portions at a flow rate of 5 ml/min. Linear gradient elution was carried out using Solvent (A), a mixture of water:acetonitrile:10% TFA=90:10:1, and Solvent (B), a mixture of water:acetonitrile:10% TFA=40:60:1, from (A):(B)=90:10 to (A):(B)=55:45 for 120 minutes. This procedure was repeated 4 times and the main peak eluted at 62–66 minute was collected. Acetonitrile was evaporated from the collected fraction and the residue was freeze-dried to obtain 25 mg of human BNP-26.

(d) Synthesis of Cys(Acm) Human BNP-32

Release from the resin and removal of the protected group was performed in the same manner as described in (b) on 700 mg protected human BNP-32 using thioanisole, TFA, TMSBr, and ethanedithiol. The product was purified over reversed phase HPLC to obtain 60.0 mg of Cys(Acm)-human BNP-32.

(e) Synthesis of Human BNP-32

60.0 mg of Cys(Acm)-human BNP-32 was subjected to the Acm removal and cyclization in the same manner as (c) using iodine to obtain 20.0 mg of crude human BNP-32. The crude product was dissolved into 4 ml of 1 N acetic acid and the solution was subjected to reversed phase HPLC over a nucleosil 120-5C18 column (20×250 mm) in 4 portions at a flow rate of 5 ml/min. Elution was carried out linear gradiently using Solvent (A), a mixture of water:acetonitrile:10% TFA=90:10:1, and Solvent (B) a mixture of water:acetonitrile:10% TFA=40:60:1, from (A):(B)=90:10 to (A):(B)=55:45 for 120 minutes. This procedure was repeated 4 times and the main peak eluted at 61–64 minute was collected. Acetonitrile was evaporated from the collected fraction and the residue was freeze-dried to obtain 5 mg of human BNP-32.

(2) Physicochemical Characteristics

Physicochemical characteristics of human BNP-26 and human BNP-32 prepared in (1) above were as follows.

(a) Form

White powder (b) Solubility in solvents

Soluble in water, acidic aqueous solutions, and acetic acid. Insoluble in chloroform, benzene, ethyl ether, and hexane.

(c) Property basic (d) Amino acid composition

Given in Table 1.

TABLE 1

| | Peptide | |
|---|---|---|
| | Human BNP-26 | Human BNP-32 |
| | Molecular Weight | |
| Amino Acid | 2793.28 | 3464.12 |
| Composition* | Measured (Calculated) | Measured (Calculated) |
| Asp + Asn | 1.06 (1) | 0.94 (1) |
| Ser | 4.61 (5) | 4.55 (6) |
| Glu + Gln | — | 0.94 (1) |
| Gly | 5.33 (5) | 4.56 (5) |
| Cys** | 1.62 (2) | 1.61 (2) |
| Val | 0.90 (1) | 1.81 (2) |
| Met | 1.02 (1) | 1.81 (2) |
| Ile | 0.94 (1) | 0.93 (1) |
| Leu | 1.98 (2) | 1.87 (2) |
| Phe | 1.00 (1) | 1.00 (1) |
| Lys | 1.97 (2) | 2.71 (3) |
| His | 1.00 (1) | 0.95 (1) |

TABLE 1-continued

| | Peptide | |
|---|---|---|
| | Human BNP-26 | Human BNP-32 |
| | Molecular Weight | |
| Amino Acid Composition* | 2793.28 Measured (Calculated) | 3464.12 Measured (Calculated) |
| Arg | 3.99 (4) | 3.78 (4) |
| Pro*** | — | 1.08 (1) |

*The measured value (mols) in the table is one example of amino acid analysis.
**Measured as Cys-SO$_3$H after the oxidation with performic acid, followed by hydrolysis. Other amino acids were hydrolyzed with 6 N HCl.
***Measured at 440 nm.

Obviously, numerous modifications and variations of the present invention are possible in light of the above teachings. It is therefore to be understood that within the scope of the appended claims, the invention may be practiced otherwise than as specifically described herein.

What is claimed is:

1. A method of producing a cDNA encoding a human brain natriuretic peptide, comprising:
   hybridizing a probe having a DNA sequence encoding a part of a porcine brain natriuretic peptide to a human cDNA library;
   selecting a positive clone; and
   isolating the cDNA of said positive clone,
   wherein said probe is obtained by digesting a complete or incomplete cDNA clone encoding porcine brain natriuretic peptide with endonucleases XhoI and RsaI.

2. The method of claim 1, wherein said probe is labeled.

* * * * *